United States Patent [19]

Lapidus

[11] 3,954,393

[45] May 4, 1976

[54] HAIR DYEING COMPOSITION CONTAINING BISMUTH CITRATE, TRIETHANOLAMINE AND SULFUR

[75] Inventor: Herbert Lapidus, Ridgefield, Conn.

[73] Assignee: Combe, Inc., White Plains, N.Y.

[22] Filed: Aug. 29, 1973

[21] Appl. No.: 392,529

[52] U.S. Cl. .................................... 8/10.1; 8/10; 8/10.2; 8/11
[51] Int. Cl.² ........................................ A61R 7/13
[58] Field of Search ................ 8/10.1, 10.2, 10, 11

[56] References Cited
UNITED STATES PATENTS

| | | | |
|---|---|---|---|
| 1,937,365 | 11/1933 | Stoddard et al. | 8/10.1 |
| 2,733,186 | 1/1956 | Brye | 8/10.2 |
| 2,763,269 | 9/1956 | Den Beste | 8/10.1 |
| 3,202,579 | 8/1965 | Berth et al. | 8/10.2 |
| 3,415,608 | 12/1968 | Tucker | 8/10.2 |

OTHER PUBLICATIONS

Winter, Handbuch der Gesamten Parfumerie und Kosmetik, Springer–Verlag, Austria, (1952), pp. 620–621, 638–639.

*Primary Examiner*—Sam Rosen
*Assistant Examiner*—Vera C. Clarke
*Attorney, Agent, or Firm*—Johnson, Dienner, Emrich & Wagner

[57] ABSTRACT

A composition for dyeing hair comprising the product formed by contacting bismuth citrate, triethanolamine and sulfur in the presence of water. The product is stable in solution; in use the product is applied to human hair, as on the scalp, and thereupon effects a darkening of the hair.

3 Claims, No Drawings

HAIR DYEING COMPOSITION CONTAINING BISMUTH CITRATE, TRIETHANOLAMINE AND SULFUR

BACKGROUND OF THE INVENTION

The invention pertains to a composition designed to be used for dyeing human hair. The composition which is in liquid form, is quite stable in that form. When applied to the hair on one's scalp, for example, the hair gradually darkens in terms of brownish tones.

I am aware that the obtention of bright yellow colors of keratinaceous materials has been disclosed in, e.g., U.S. Pat. No. 2,719,104, those colors being obtained through use of a water soluble salt of bismuth, namely bismuth nitrate. To achieve brown colors, according to this prior art, white wool yarn is dyed with mixtures of bismuth and nickel, the depth of brown color being controlled by varying proportions of water soluble bismuth salts which produces the bright yellow color, and water soluble nickel salts which produce a deep brown.

SUMMARY OF THE INVENTION

The present invention is directed to the provision of a hair dyeing composition which, in use, produces desirable shades of brown when applied to human hair. It is not necesssary to use a plurality of metal salts to achieve this, and in accordance with my invention I have found that a composition comprising the product formed by contacting bismuth citrate, triethanolamine and sulfur, in the presence of water when applied to human hair results in pleasing shades of brown. I am not certain of the precise nature of the composition which is produced, as will be hereinafter fully disclosed, in accordance with the procedural aspects of my invention, although it appears as though some kind of complex is formed between the bismuth citrate, triethanolamine and sulfur.

I am likewise uncertain as to why my composition results in brown coloration of hair since one would expect, from the teaching of the aforesaid U.S. Pat. No. 2,719,104 that bismuth salts would result in production of bright yellow colors when applied to hair.

Bismuth citrate, which is one of the essential components in my novel composition, is water-insoluble, as is sulfur, another essential component. The third essential component in my composition, triethanolamine, appears to function as a complex-forming material when contacted with the bismuth citrate, resulting in a solution. The said solution is quite stable while it is in solution form and in the presence of sulfur, i.e., in the bottle or other container, without undesirable precipitation occurring. When applied to the hair, there appears to take place some form of chemical reaction influenced by the keratinaceous nature of hair, and the various products which are naturally on the hair such as oils and the like, manifested in part by darkening of the hair in shades of brown.

In preparing my novel hair dyeing composition I mix together, in a suitable container, triethanolamine, propylene glycol, alcohol and water, and then add thereto bismuth citrate and polyvinylpyrrolidone. The entire mix is then heated slowly until a clear solution is obtained. Meanwhile, a mixture of sulfur and a wetting agent is prepared by grinding sulfur, wetting agent and water in a separate container until the sulfur has been reduced to fine powder. After the first-above described clear solution has cooled to room temperature, the ground mixture of sulfur, wetting agent and water is added thereto. The resulting composition is then ready for use by applying it to the hair.

DESCRIPTION OF THE PREFERRED EMBODIMENT

In order to more clearly disclose my invention, a specific example illustrating the preparation of a presently preferred embodiment of the invention will be described hereinafter. It should be understood that the following description is done solely for purposes of illustration and is not intended to limit the scope of the invention except as may be required by the appended claims.

Example I

| Ingredients | Percent (by weight) |
| --- | --- |
| Bismuth Citrate (USP Powder) | 0.25% |
| Propylene Glycol (USP) | 10.00 |
| Triethanolamine (98%) | 3.00 |
| Triton X 100 (Rohm & Haas) | 0.50 |
| Alcohol SD-40 | 10.00 |
| Polyvinylpyrrolidone (K-30.GAF) | 0.32 |
| Sulfur, Precipitated | 0.25 |
| Water | 75.68 |

The foregoing components are incorporated into the composition of my invention as follows: 70 parts of the 75.68 parts of water are measured into a sufficiently large stainless steel kettle. The propylene glycol, triethanolamine and alcohol are then added to the water. The bismuth citrate and polyvinylpyrrolidone are then added slowly with mixing. The entire mix is then heated slowly until a clear solution is obtained (45°–50°C). In a separate container the sulfur, Triton X 100 and the remaining portion of the water are ground together until the sulfur has been reduced to a uniform and fine powder. If it is desired to incorporate a perfume, this is added to the Triton X 100 before grinding with sulfur. The original water solution is cooled, and the previously described ground powder mix is added thereto, with stirring.

Triton X–100 is the condensation product of iso octyl pheyl polyethoxy ethanol with 9-10 mols of ethylene oxide (Detergents and Emulsifiers. Annual, 1963- McCutheon.)

While bismuth citrate, triethanolamine and sulfur are essential components of the compositon of my invention, it is to be understood that the obvious and well known equivalents of the other components may be substituted for the preferred ones listed in the foregoing example.

And since it is obvious that many modifications and variations in the nature and proportions of the aforesaid ingredients may be made without departing from the spirit and scope of the invention, only such limitations should be imposed as are indicated in the appended claims.

I claim:

1. A hair dyeing composition comprising an effective amount of sulfur and the water soluble reaction product of bismuth citrate and triethanolamine in an aqueous vehicle.

2. A hair dyeing composition comprising an aqueous vehicle containing 0.25 parts of sulfur, and an effective amount of the product formed by reacting 0.25 parts bismuth citrate with 3.0 parts triethanolamine.

3. A hair dyeing composition comprising in percent by weight 0.25% bismuth citrate, 10.00% propylene glycol, 3.00% triethanolamine (98%), 0.50% of the condensation product of iso octyl phenyl polyethoxy ethanol with 9–10 mols of ethylene oxide, 10.00% ethyl alcohol, 0.32% polyvinyl pyrrolidone, 0.25% sulfur and 75.68% water.

* * * * *